United States Patent [19]

Kazuo

[11] Patent Number: 5,310,684

[45] Date of Patent: May 10, 1994

[54] REAGENT FOR DETECTING OCCULT BLOOD

[76] Inventor: Tabata Kazuo, 22-21 Kamishijyocho, Higashiosaka-shi, Osaka-fu 579, Japan

[21] Appl. No.: 876,739

[22] Filed: Apr. 27, 1992

[30] Foreign Application Priority Data

Apr. 27, 1991 [JP] Japan .................. 3-191374

[51] Int. Cl.$^5$ .............................. G01N 21/75
[52] U.S. Cl. ...................... 436/166; 436/66; 436/501
[58] Field of Search ................ 436/166, 66, 501

[56] References Cited

U.S. PATENT DOCUMENTS

| | | | |
|---|---|---|---|
| 4,647,541 | 3/1987 | Guadagno et al. | 436/166 |
| 4,857,457 | 8/1989 | Shamsuddin et al. | 436/501 |
| 4,965,210 | 10/1990 | Modrovich | 436/166 |
| 5,081,040 | 1/1992 | Patel et al. | 436/66 |

FOREIGN PATENT DOCUMENTS 63-247659  2/1989  Japan .

OTHER PUBLICATIONS

The Merck Index, 10th edition, p. 3486.

*Primary Examiner*—James C. Housel
*Assistant Examiner*—Rachel Freed
*Attorney, Agent, or Firm*—Koda and Androlia

[57] ABSTRACT

A reagent to be used in detection of occult blood comprising a mixed solution of sodium carbonate, 3-amino phthalic acid hydrazide, and iron and sodium derivative of ethylenediaminetetraacetic acid, and hydrogen peroxide.

1 Claim, No Drawings

REAGENT FOR DETECTING OCCULT BLOOD

BACKGROUND OF THE INVENTION

1. Field of the Invention

The present invention relates to a reagent for detecting occult blood contained in human feces or urine (hereinafter called excretion).

2. Prior Art

It is hard to detect grossly the occult blood which is a trace hemorrhage in the human digestive tract or urinary organ. If the occult blood is detected, however, ulcer or tumor of digestive tract, infection of urinary tract, stone, tumor, blood disease or other intractable diseases may be detected in an early stage before advanced too much in symptoms, so that the progress of refractory diseases may be prevented.

Therefore, the occult blood reaction for detecting whether occult blood is contained in feces or other excretion or not has been attempted hitherto in various manners. Among such manners, catalyst have commonly been used. The principle of these manners is as follows.

That is, (a) acetic acid is caused to act in the hemoglobin in blood to form hematin acetate, and by making use of its catalytic action, the reagent such as orthotoluidine, phenolphthalein, benzidine and guaiacol acid is oxidized by hydrogen peroxide, and the occult blood is determined by the developed color.

(b) Aside from such catalytic method, recently, computer-assisted diagnostic apparatus have been developed to attempt early discovery of focus.

In the catalytic method (a), however, the reagent includes carcinogenic substance such as benzidine.

In the computer apparatus (b), a huge system is needed and it is very costly, and aside from the economical reason for patients, specialists were necessary to interpret the results of computer diagnosis.

SUMMARY OF THE INVENTION

It is hence a primary object of the invention to present a reagent for detecting occult blood that is simple, handy and inexpensive, without using the catalytic method or computer system.

By using the reagent for detection occult blood of the invention, if the excretion was free from occult blood, the color of the excretion is unchanged, and foams are hardly noted, and the temperature declines. In contrast if the excretion contains occult blood, the excretion turns to a pink-tinted violet color, and foams build up and the temperature rises, so that the presence or absence of occult blood may be judged anytime, anywhere, by anyone, in hospital or at home, easily, safely and inexpensively, so that it is outstandingly effective to discover disease at an early stage until the symptom is advanced.

Besides, unlike the conventional method of sampling a trace from the excretion, the whole excretion discharged by a human is tested, and the precision of examination is improved.

To achieve the above object, the invention presents a reagent for detecting occult blood which comprises a mixed solution of sodium carbonate, 3-amino phthalic acid hydrazide, and iron and sodium derivative of ethylenediaminetetraacetic acid (tradename CLEWAT, hereinafter also called iron and sodium derivative of EDTA), and hydrogen peroxide.

The hydrogen peroxide may be used by mixing into the mixed solution before use.

By mixing the reagent in the whole volume of the feces and urine (excretion) discharged by a human, presence or absence of occult blood (black blood) is detected.

DETAILED DESCRIPTION OF THE INVENTION

Some examples of the invention are described in detail below.

EXAMPLE 1

| (1) A mixed solution was obtained by putting | |
| --- | --- |
| Sodium carbonate | 6.5 g |
| 3-Amino phthalic acid hydrazide | 0.2 g |
| Iron and sodium derivative of ethylenediaminetetraacetic acid (iron and sodium derivative of EDTA) | 7.0 g |
| into a container containing 185 cc of aqueous solution. | |

(2) 31.3 g of hydrogen peroxide was separately prepared in order to put into the container filled with the mixed solution of (1) at the time of detection of occult blood.

| (3) Samples A and B were prepared. | |
| --- | --- |
| A: Feces and urine mixture without occult blood | 388 g |
| B: Feces and urine mixture with occult blood | 488 g |

(4) Samples A and B were put in measuring cylinders of 5 cm in diameter and about 30 cm in height, and the whole volume of reagent mixing the mixed solution and hydrogen peroxide of (1) and (2) was added in each measuring cylinder.

EXAMPLE 2

| (1) A mixed solution was obtained by putting | |
| --- | --- |
| Sodium carbonate | 9.0 g |
| 3-Amino phthalic acid hydrazide | 0.1 g |
| Iron and sodium derivative of ethylenediaminetetraacetic acid (iron and sodium derivative of EDTA) | 6.0 g |
| into a container containing 160 cc of aqueous solution. | |

(2) 29.3 g of hydrogen peroxide was separately prepared in order to put into the container filled with the mixed solution of (1) at the time of detection of occult blood.

| (3) Samples A and B were prepared. | |
| --- | --- |
| A: Feces and urine mixture without occult blood | 840 g |
| B: Feces and urine mixture with occult blood | 440 g |

(4) Samples A and B were put in measuring cylinders of 5 cm in diameter and about 30 cm in height, and the whole volume of reagent mixing the mixed solution and hydrogen peroxide of (1) and (2) was added in each measuring cylinder.

EXAMPLE 3

| (1) A mixed solution was obtained by putting | |
| --- | --- |
| Sodium carbonate | 7.2 g |
| 3-Amino phthalic acid hydrazide | 0.2 g |

-continued

| (1) A mixed solution was obtained by putting | |
|---|---|
| Iron and sodium derivative of ethylenediaminetetraacetic acid (iron and sodium derivative of EDTA) into a container containing 195 cc of aqueous solution. | 7.2 g |

(2) 33.3 g of hydrogen peroxide was separately prepared in order to put into the container filled with the mixed solution of (1) at the time of detection of occult blood.

| (3) Samples A and B were prepared. | |
|---|---|
| A: Urine without occult blood | 242.5 cc |
| B: Urine with occult blood | 420 cc |

(4) Samples A and B were put in measuring cylinders of 5 cm in diameter and about 30 cm in height, and the whole volume of reagent mixing the mixed solution and hydrogen peroxide of (1) and (2) was added in each measuring cylinder.

EXAMPLE 4

| (1) A mixed solution was obtained by putting | |
|---|---|
| Sodium carbonate | 5.0 g |
| 3-Amino phthalic acid hydrazide | 0.1 g |
| Iron and sodium derivative of ethylenediaminetetraacetic acid (iron and sodium derivative of EDTA) into a container containing 185 cc of aqueous solution. | 4.0 g |

(2) 27.3 g of hydrogen peroxide was separately prepared in order to put into the container filled with the mixed solution of (1) at the time of detection of occult blood.

| (3) Samples A and B were prepared. | |
|---|---|
| A: Urine without occult blood | 291 cc |
| B: Urine with occult blood | 391 cc |

(4) Samples A and B were put in measuring cylinders of 5 cm in diameter and about 30 cm in height, and the whole volume of reagent mixing the mixed solution and hydrogen peroxide of (1) and (2) was added in each measuring cylinder.

As known from the above examples, the mixing ratio of the reagent is satisfactory in the range of:

| | |
|---|---|
| 3-Amino phthalic acid hydrazide | 0.2–0.5% |
| Sodium carbonate | 13–19% |
| Iron and sodium derivative of ethylenediaminetetraacetic acid (iron and sodium derivative of EDTA) | 10–17% |
| Hydrogen peroxide | 66–75% |

However, by using 3-amino phthalic acid hydrazide within 1%, other components may be properly changed.

In samples A and B of the examples, the color change, foaming, and temperature changes were as follows.

1. Color change
   A: The color change could not be recognized visually, and the excretion color was almost unchanged.
   B: In 2 minutes after contact of the reagent with the excretion, a pink-tinted violet color developed, and it returned to the original color in about 12 minutes.
2. Foaming change
   A: Foams were hardly noted in any example.
   B: In Examples 1 and 2, in 8 minutes after start of test, the foaming maintained maximum height of 29 cm in the measuring cylinder.
   In Examples 3 and 4, in 8 minutes after start of test the foaming maintained maximum height of 21 cm in the measuring cylinder.
3. Temperature change
   A: In Examples 1 and 2, the temperature reached 31° C. in 8 minutes after start of test. In Examples 3 and 4, the temperature reached 26° C. in 8 minutes after start of test.
   B: In Examples 1 and 2, the temperature reached 37° C. in 8 minutes after start of test. In Examples 3 and 4, the temperature reached 34° C. in 8 minutes after start of test.

The color of excretion varies with the kind of food taken, and the mixing amount of the reagent of the invention varies with the volume of the excretion to be examined.

Besides, the detected temperature varies somewhat depending on the content of the iron and sodium derivative of EDTA, and the blending ratio of hydrogen peroxide.

Thus, between samples A and B, the result of experiment is obviously different. As this reason, the following point may be considered although they are not logically proved yet.

The sodium carbonate in the reagent is considered to increase the pH of the reagent to turn the reagent alkaline, thereby assisting the coloring of the coloring matter (nitrogen carbonate compound).

Human erythrocyte components are destroyed by hydrogen peroxide, and the iron content in the destroyed erythrocytes is chelated by EDTA.

The chelate compound is destroyed by hydrogen peroxide, and the iron and reagent react to present a pink-tinted violet color.

If occult blood is present in the sample, the hydrogen peroxide in the reagent acts on the erythrocyte components and chelate compound as mentioned above. The hydrogen peroxide destroys erythrocyte components and at the same time generates oxygen to build up foams, thereby raising the temperature.

The reagent of the invention should be preferably kept at 2 to 5° C. by storing, for example, in a refrigerator in order to maintain the quality for a long period.

Besides, in order to clarify the presence of occult blood by using the reagent of the invention, it is recommended to abstain from fish and meat considering the effects of other animal proteins for two or three days before examination.

It is, meanwhile, possible to examine in a small-free atmosphere by mixing 3-amino phthalic acid hydrazide, sodium carbonate and iron and sodium derivative of EDTA, dissolving sufficiently, adding hydrogen peroxide water, and adding the mixed solution to the excretion and stirring to make the excretion odorless.

I claim:
1. A reagent for detecting occult blood comprising a mixed solution of sodium carbonate, 3-amino phthalic acid hydrazide, and iron and sodium derivative of ethylene-diaminetetraacetic acid, and hydrogen peroxide.

* * * * *